(12) United States Patent
Luther et al.

(10) Patent No.: US 9,522,079 B2
(45) Date of Patent: Dec. 20, 2016

(54) FILTER WITH AN EXTENSION ELEMENT

(75) Inventors: Preben Luther, Bikerød (DK); Lars Olav Schertiger, Fredensborg (DK); Jan Torstensen, Virum (DK)

(73) Assignee: Coloplast A/S, Humlebaek (DK)

( * ) Notice: Subject to any disclaimer, the term of this patent is extended or adjusted under 35 U.S.C. 154(b) by 420 days.

(21) Appl. No.: 13/701,513

(22) PCT Filed: Jun. 1, 2011

(86) PCT No.: PCT/DK2011/050190
§ 371 (c)(1),
(2), (4) Date: Dec. 3, 2012

(87) PCT Pub. No.: WO2011/150937
PCT Pub. Date: Dec. 8, 2011

(65) Prior Publication Data
US 2013/0072885 A1    Mar. 21, 2013

(30) Foreign Application Priority Data

Jun. 4, 2010 (DK) .......................... PA 2010 70245

(51) Int. Cl.
| A61F 5/441 | (2006.01) |
| A61F 5/44 | (2006.01) |
| A61F 5/445 | (2006.01) |

(52) U.S. Cl.
CPC ............ *A61F 5/441* (2013.01); *A61F 5/4404* (2013.01); *A61F 5/445* (2013.01)

(58) Field of Classification Search
USPC ....................................................... 604/333
See application file for complete search history.

(56) References Cited

U.S. PATENT DOCUMENTS

| 4,387,712 | A | | 6/1983 | Briggs et al. |
| 5,250,042 | A | * | 10/1993 | Torgalkar ................ A61F 5/441 604/333 |
| 5,306,264 | A | | 4/1994 | Ferguson et al. |
| 6,135,986 | A | * | 10/2000 | Leisner ................... A61F 5/441 604/322 |
| 2004/0059306 | A1 | * | 3/2004 | Tsal ...................... A61F 5/4404 604/332 |
| 2005/0070863 | A1 | * | 3/2005 | Bulow .................... A61F 5/441 604/332 |
| 2007/0207186 | A1 | * | 9/2007 | Scanlon .................... A61F 2/07 424/424 |

(Continued)

FOREIGN PATENT DOCUMENTS

| CN | 1551750 | 12/2004 |
| DE | 20021420 | 4/2001 |

(Continued)

*Primary Examiner* — Adam Marcetich
*Assistant Examiner* — Guy K Townsend
(74) *Attorney, Agent, or Firm* — Coloplast Corp., Coloplast A/S; Nick Baumann

(57) ABSTRACT

An ostomy bag with a filter construction is provided. The filter construction includes a deodorising element and an extension element. The extension element may function to provide buoyancy means so that a gas-inlet portion at the extension element is kept on top of the output or pushed away by the output. The extension element may also be attached to the ostomy bag at a distance from the deodorising element so as to provide a controlled flow path for the gas-flow.

16 Claims, 4 Drawing Sheets

(56) References Cited

U.S. PATENT DOCUMENTS

| | | | | |
|---|---|---|---|---|
| 2009/0227973 A1* | 9/2009 | Worsoee | ............... | A61F 5/441 604/333 |
| 2013/0072885 A1* | 3/2013 | Luther | ............... | A61F 5/4404 604/333 |
| 2013/0072886 A1* | 3/2013 | Schertiger | ............... | A61F 5/441 604/333 |
| 2013/0218111 A1* | 8/2013 | Schertiger | ............... | A61F 5/441 604/333 |

FOREIGN PATENT DOCUMENTS

| | | |
|---|---|---|
| EP | 443728 | 8/1991 |
| EP | 607028 | 7/1994 |
| EP | 981311 | 3/2000 |
| GB | 2124086 | 2/1984 |
| WO | 03020188 | 3/2003 |
| WO | WO03020188 | 3/2003 |
| WO | 2006048019 | 5/2006 |
| WO | 2007000168 | 1/2007 |

\* cited by examiner

FILTER WITH AN EXTENSION ELEMENT

The invention relates to a filter for use in an ostomy bag. The filter has an extension element so that the inlet is placed a distance from the deodorising element.

BACKGROUND

In connection with surgery for a number of diseases in the gastro-intestinal tract, one of the consequences in many cases is that the patient is left with an abdominal stoma such as a colostomy, an ileostomy or a urostomy in the abdominal wall for the discharge of visceral contents. The discharge of visceral contents including intestinal gases cannot be regulated at will. For that purpose, the user will have to rely on an appliance to collect the material emerging from such opening in a bag, which is later emptied and/or discarded at a suitable time.

The discharge of flatus, measured in volume, may exceed the discharge of solid and liquid faecal matter by many hundreds of percent and therefore there is usually the need for the continuous or frequent venting of the intestine or the collecting bag. Normally the outflowing flatus is deodorised with a suitable filter. Commonly, the active filter is powdered active carbon, which absorbs $H_2S$ being the principal component of the smell of flatus.

During use of a collecting bag, the output from a colostomy or an ileostomy may stick on the face of the filter facing inwards in the collecting bag. This will eventually lead to clogging of the filter thereby reducing the flow through the filter. When the filter is completely blocked, it will stop functioning and the bag will fill with gases and expand, an effect also known as ballooning. This may cause embarrassment for the user because the bag will be noticeable under the clothing. It may also lead to the bag being detached from the wafer, in case a two-piece appliance is used, or being detached from the skin, in case a one-piece appliance is used.

DESCRIPTION OF RELATED ART

International application no. WO2006/048019 relates to an in situ cleanable filter for an ostomy appliance comprising a pathway for leading gases to a vent in an ostomy bag and a protective element contained in said pathway to prevent solid or semi-liquid waste from blocking the pathway. The protective element is made of an open celled compressible material having a memory and having a pore size of at least 60 PPI.

European Patent no. EP0607028B relates to an ostomy bag including a multi-stage filter system that provides contamination protection for a deodorizing filter in the system. The multi-stage filter system also includes a gas transmissible protection filter that is impassable to semi-liquid waste material. The protection filter is located in the ostomy bag to precede the deodorizing filter such that gaseous waste must pass through the protection filter before it passes through the deodorizing filter.

German utility model no. DE20021420U relates to an ostomy bag with an inlet, a gas discharge opening where the gas discharge opening is placed upstream of the filter. The filter consists of a rod-shaped hollow body filled with a filtering medium.

SUMMARY OF THE INVENTION

The invention relates to an ostomy bag with a filter construction. The ostomy bag has a front wall and a rear wall. The filter construction has a deodorising element and an extension element. The extension element has a gas-inlet portion which is provided with numerous gas-inlets placed across an outer surface of the extension element. Thereby it is ensured that at least one of the gas-inlets is always out of contact with the output.

DETAILED DESCRIPTION OF THE INVENTION

In a first aspect, the invention relates to an ostomy bag comprising
  a pouch including a front wall and a rear wall
  a waste inlet opening in the rear wall for letting the output from the stoma enter into the pouch,
  a vent opening in either the front wall or the rear wall for letting gas exit the bag,
  a filter construction with a gas-outlet in alignment with the vent opening,
  the filter construction including a deodorising element and an elongated extension element providing an enclosure for gas-flow,
  the deodorising element being provided with the gas outlet,
  the deodorising element being connected to a first end of the elongated extension element, the extension element being provided with a second end so that the direction from the first end to the second end defines the longitudinal direction of the extension element,
  the extension element having a gas-inlet portion including a number of gas-inlets to the filter construction,
  the gas-inlets being placed across an outer surface of the extension element in the transverse direction so that the gas-inlets generally face in the opposite directions from the outer surface.

The extension element in the filter construction provides gas-inlets away from the deodorising element. Thus there is a distance between the closest gas-inlet and the deodorising element. Therefore, the extension element may function as a kind of pre-filter, making the liquid and semi-solid matter travel a longer distance before potentially reaching the deodorising element.

An ostomy bag is well-known in the art. It usually comprises a front wall and a rear wall of gas- and liquid impermeable foil-material (for example of polyethylene (PE), polyvinyl-chloride (PVC) or ethylene-vinyl-acetate (EVA)) that is welded or glued around the edges or the rim so as to form a waste collection chamber. The bag may be welded or glued only partly around the rim so that an opening for emptying the bag is provided in the lower end. In that case the bag may be provided with means for closing that opening. The bag includes a waste inlet opening which at the outer side is provided either with mechanical or adhesive coupling means for coupling to a body side wafer or with a skin-friendly adhesive adapted for direct adhering to the abdomen of the user.

Usually, the waste inlet opening is placed in the upper part of the ostomy bag so that when a user stands up, the waste inlet opening will be above the midline of the ostomy bag. This leaves a larger collecting volume below the waste inlet opening. Thus the top of the ostomy bag is defined as the part closest to the waste inlet opening, and the bottom is defined as the opposite part.

The vent of the ostomy bag may be placed either in the contour or the rim of the bag—by leaving a small part of this un-welded, or it may be placed as a separate hole in the front or rear wall of the bag.

The extension element is attached to the deodorising element. It provides an enclosure for the gas-flow which may be in the form of a tube element so as to allow for gas-flow through the tube from the gas-inlet portion including the gas-inlets to the deodorising element. It is an elongated element having a first end connected to the deodorising element and a second end opposite in the longitudinal direction. The gas-inlets being placed facing in opposite directions has the effect that no matter how the extension element is positioned, at least one of the gas-inlets is always accessible for entry of gas.

In an embodiment of the invention, the extension element includes buoyancy means. In this embodiment, the extension element is only attached to any part of the ostomy bag in the first end, where it is attached to the deodorising element. Therefore, the remaining part of the extension element may float around freely in the bag. Because the extension element is made of material having a lower density than the output, the extension element will float atop the output. The theory is that with output from an ileostomy (which usually is rather thin, having a syrupy consistency) at least a part of the extension element will float "on top" of the output. With output from a colostomy (which usually is thicker, like porridge) the element will simply be pushed away. The extension element will thus never be covered completely by output and at least part of the gas-inlet portion is not covered in output for example the part facing upwards from the output, if the extension element floats atop the output. Therefore, at least some of the gas-inlets will never be completely covered and prevent the filter construction from being completely clogged and thus allow gas flow.

The extension element may include buoyancy means in form of a foil-element or an element made of non-woven material. The foil-material may be the type of foil-material regularly used for filters for ostomy bags, for example styrene-ethylene-butadiene-styrene (SEBS) and a mixture of poly-ethylene (PE) and ethylene-vinyl-acetate (EVA). Non-woven materials may be of the type regularly used for covering the surface of the ostomy bag on the outside, for example poly-ethylene (PE), poly-propylene (PP) or Poly-ester. All of these types of material are cheap and cooperate well with the other materials in an ostomy bag.

The extension element may be made by two elongate foil-elements welded together at their sides (and at the second end) so as to provide an enclosure between them. It may also be made by one foil-element folded upon itself and welded at the side and at the second end so as to provide an enclosure. It may be folded to provide an edge or folded to provide a tube-element.

In the above-mentioned embodiments, air enclosed in the foil-element may function as buoyancy means.

In an embodiment, foam material may be enclosed in the foil-element or the non-woven element. Thereby the foil-element or non-woven element is prevented from collapsing completely if it is bent due to the user's body movement. Thus, there will always be pathway through the extension element for the gas flow towards the deodorising element. The foam may function as a further pre-filtering mechanism as it is able to capture liquid and semi-solid material entering into the extension element.

In another embodiment, the extension element may be in form of a tube-element made of a rather rigid material, for example PE. The tube-element will not be likely to collapse during use. The tube-element may be provided with corrugations so as to enhance the comfort for the user and to prevent the tube from penetrating through the ostomy bag.

One of the decisive factors for the buoyancy is the density of the extension element when compared to the density of the output in which the extension element is to be present. To keep the extension element afloat it must be made of a material with a density lower than the density of the output.

The density of most plastics is below 1000 kg/m$^3$. As an example the density of SEBS-foil is approximately 900 kg/m$^3$. The plastics may in use enclose air, thus lowering the density of the extension element.

The density of the foam material may be as low as 20 kg/m$^3$.

In another embodiment, the buoyancy means is a buoyant element that is attached at the second end. This buoyant element may include a foam element enclosed in foil material. In this embodiment, the extension element itself may be made of any material, because the buoyancy will be provided by a separate element. The buoyant element has to be able to provide enough buoyant force to keep the gas-inlet portion of the extension element afloat. The buoyancy force required depends on how much the bag is tilted around and squeezed during wear. It is contemplated that a buoyancy force of about 0.01 N will be enough in most situations. Tests have shown that a foam material of polyurethane (PU) with 45 PPI will provide enough buoyancy force if the foam is larger than 5 mm×10 mm×10 mm. PPI is a unit giving a measure for the pore size although it actually refers to number of pores per inch in the foam material.

The length of the extension element influences how the element can be pushed away by or is able to float atop the output. The distance between the first end of the extension element and the end of the gas-inlet portion closest to the first end has to be so long that the gas-inlets can be kept open, even if the output gets very close to the deodorising element. Thus, there is a non-permeable portion of the surface of the extension element without gas-inlets. Tests have shown that if this distance is at least 3 cm, then the inlets will be kept open. That the surface is non-permeable means that it is gas- and liquid impermeable in the conditions normally occurring in an ostomy bag.

In another embodiment, the second end of the extension element is attached to the ostomy bag at a distance from the deodorising element. Attaching the extension element at a certain distance from the deodorising element allows a controlled distance between the gas-inlet portion of the extension and the deodorising element and thus a controlled distance between the gas-inlets and the deodorising element.

Sometimes output from a colostomy has such a consistency that it does not readily fall towards the bottom of the pouch but rather stays in the upper volume of the pouch near the waste inlet opening. For such situations, it may be an advantage if the gas-inlet to the filter construction is placed in the lower half of the pouch. This is possible with an extension element, where the second end is attached in the lower half of the pouch, below the midline—that is the part of the pouch lying below the waste inlet opening in the normal use situation.

For one-piece ostomy bags—that is ostomy bags provided with a skin friendly adhesive around the waste inlet opening for attaching the bag to the abdomen of the user—the user typically adapts the wafer to the size and shape of the stoma. For such use it is an advantage if the second end of the extension element is attached so that the extension element is positioned distant from the waste inlet opening in a plane transverse to the walls of the ostomy bag. In other words, the entire filter construction may be positioned away from the volume of the bag immediately surrounding the waste inlet opening. This way the risk of cutting into the filter construction when cutting the wafer is minimised. The extension element may be kept within 2-5 cm from the rim of the pouch. The filter construction may have a rather sharp edge in some embodiments, for example where two foils are welded together to form the extension element. It may be an advantage if this edge is kept at least a few millimetres radially beyond the maximum cutting diameter of the waste inlet opening. This is to minimise the risk of the sharp edge irritation the stoma if the stoma were to enter into the ostomy bag.

Filters for ostomy bags contain an element providing the deodorising effect of the gas passing through the filter. This is the so-called deodorising element. Typically this element is a foam-element that is impregnated with carbon. The deodorising element is usually enclosed in foil-material and provided with at least one inlet and at least one outlet. The deodorising element enclosed in foil and provided with an inlet and outlet constitutes the actual deodorising filter. An example of such a deodorising filter is described in European Patent no. EP0981311 B1. Another example is a deodorising filter sold under the trademark "Filtrodor"®. The outlet of the deodorising filter will be a gas outlet which is in communication with the ambience outside the bag through the vent opening.

DETAILED DESCRIPTION OF THE DRAWING

Figure 1:
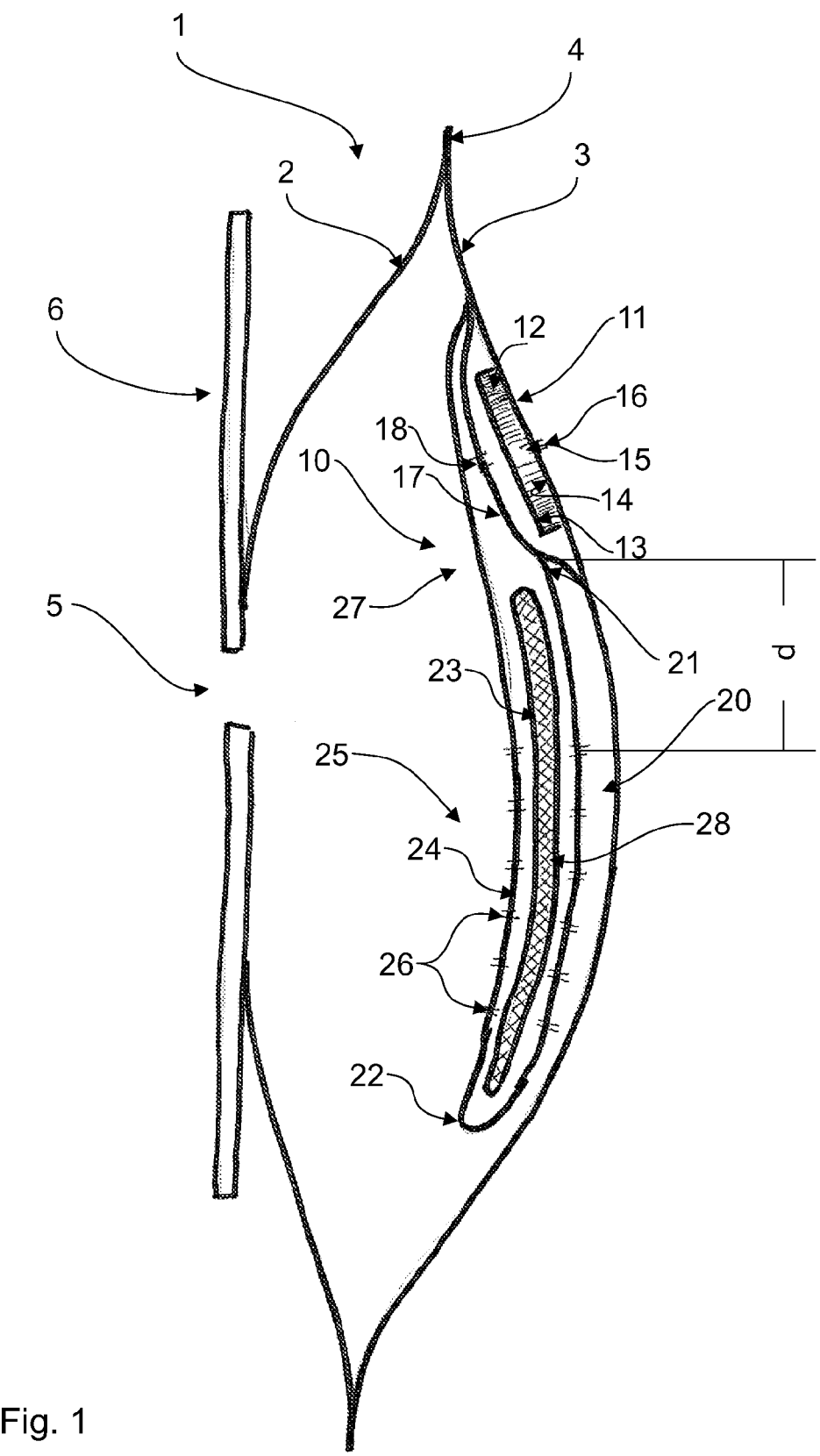
FIG. 1 illustrates an ostomy bag according to the invention.

FIG. 1 illustrates an ostomy bag 1 according to the invention. The ostomy bag comprises a rear wall 2 and a front wall 3, that are welded together along their rim 4. The rear wall 2 has a waste inlet opening 5, which in this embodiment is surrounded by a skin-friendly adhesive 6. The filter construction 10 in the ostomy bag comprises a deodorising element 11 and an elongate extension element 20. The deodorising element 11 is disc-shaped and comprises foam impregnated with carbon 12 covered by two gas-impermeable foils 13, 14. The foil 14 facing the front wall 3 is provided with a gas outlet 15 placed in alignment with the vent 16 in the front wall. The deodorising element 11 including the cover-foils 13, 14 is further enclosed in an enclosure foil 17 provided with an inlet 18 to the deodorising element. Thus, gas coming from the extension element enters through the inlet 18 in the enclosure foil 17 and from there around the deodorising element 11 to enter into the carbon-impregnated foam 12 at the periphery, radially through the element 11 towards the centre and exits through the gas-outlet 15 and the vent 16.

The extension element 20 comprises a first end 21 and a second end 22 and an enclosure 23 in between. In this embodiment, the enclosure 23 is provided by a foil layer 24 that is welded at a side (not shown) and at the second end 22. The foil layer 24 is perforated over a part of the surface so that the extension element 20 is divided into a gas-inlet portion 25 with gas-inlets 26 and a non-permeable portion 27 without gas-inlets.

Thus, there is a distance d between the gas-inlet closest to the deodorising element and the first end of the extension element. In this embodiment, the enclosure 23 further includes a foam-element 28, which may function as a further stopper for liquid entering into the extension element and as an element preventing kinking of the extension element.

Figure 2:
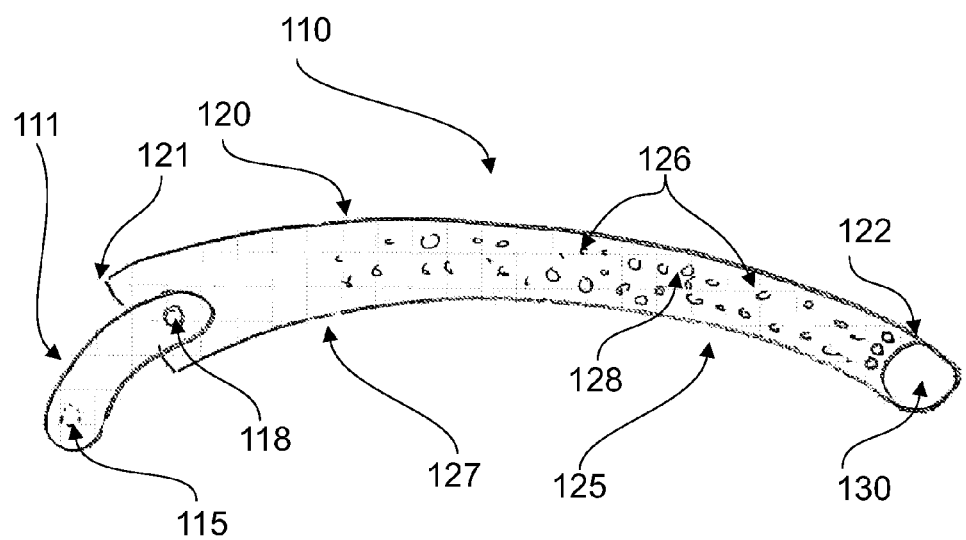
FIG. 2 illustrates an extension element that may be used in an ostomy bag according to the invention.

FIG. 2 illustrates another filter construction 110 for use in an ostomy bag according to the invention. The filter construction 110 includes a deodorising element 111 and an elongated tube-like extension element 120. The deodorising element 111 includes a gas-outlet 115, which in use is positioned in an aligned position with the vent of the ostomy bag (not shown). In this embodiment, the deodorising element 111 further includes an inlet 118. The extension element 120 is connected to the deodorising element 111 at a first end 121 and stretches in a generally longitudinal direction towards a second end 122. In the embodiment shown, the extension element 120 includes foam 128 enclosed inside the enclosure 123 of the extension element. At the second end 122 a buoyant element 130 is attached to the extension element 120. Like with the embodiment in FIG. 1, the extension element 120 has perforations providing gas-inlets 126 at a gas-inlet portion 125. Again, there is a non-permeable portion 127 closest to the deodorising element 111.

Figure 3:
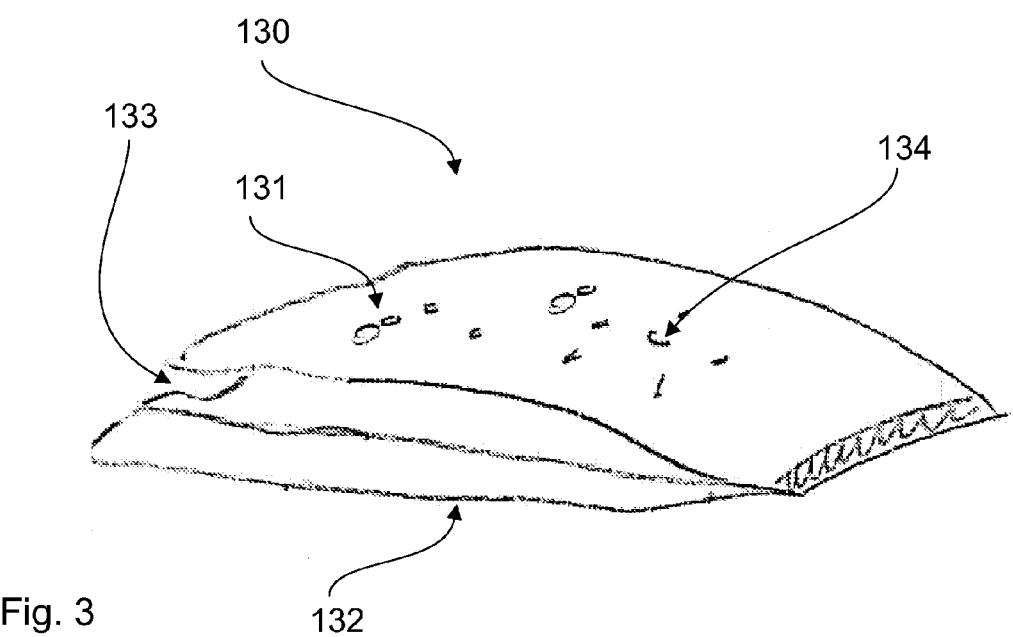
FIG. 3 illustrates a separate buoyant element.

FIG. 3 illustrates a buoyant element 130. This buoyant element 130 consists of two foil layers 131, 132 that are welded together to form a chamber 133 for a piece of foam 134.

Figure 4:
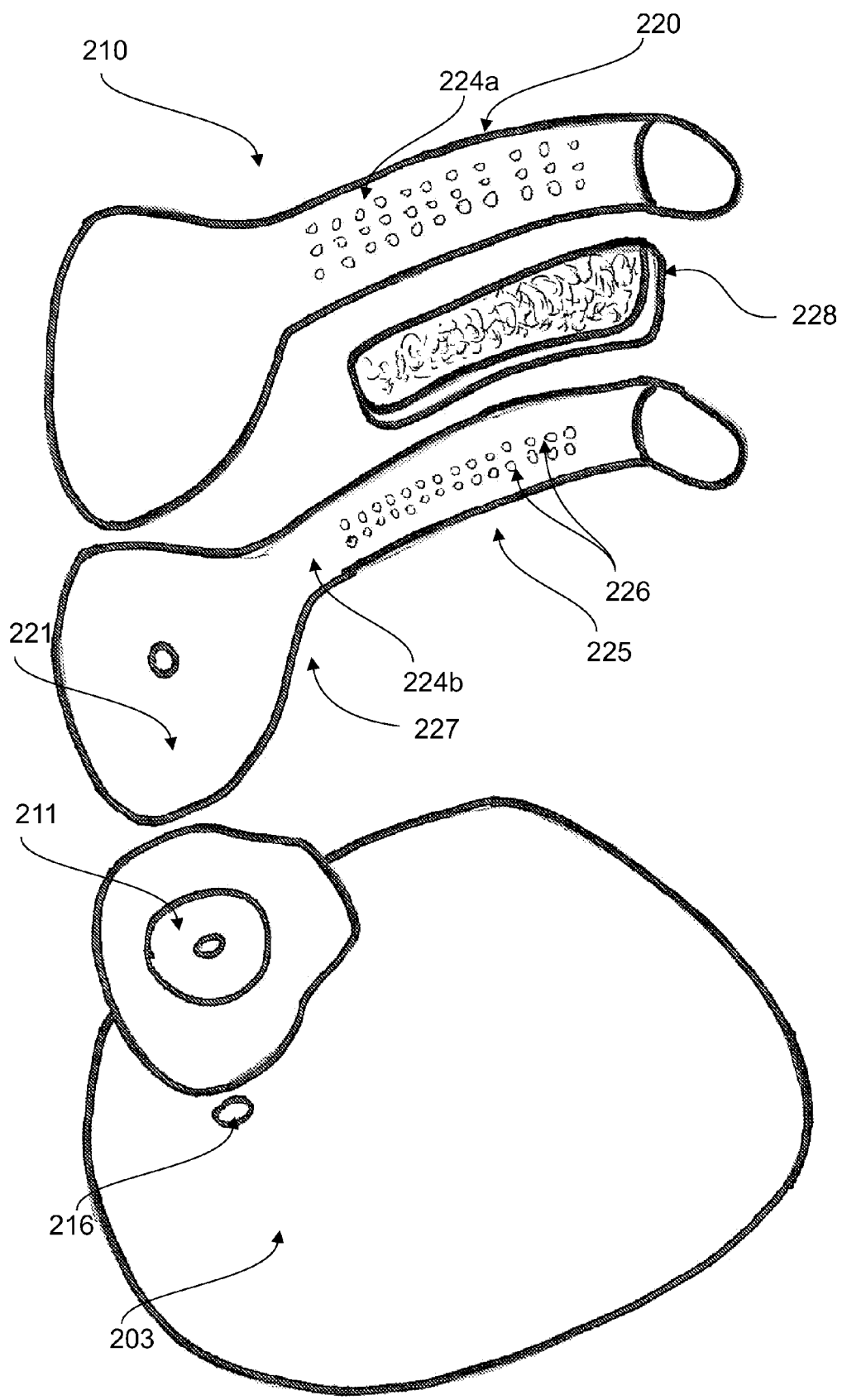
FIG. 4 illustrates an exploded view of an extension element.

FIG. 4 illustrates how a filter construction 210 can be positioned in alignment with the vent 216 in a wall 203 of an ostomy bag. The deodorising element 211 is, in this embodiment, circular—therefore the connection at the first end 221 between the extension element 220 and the deodorising element 211 is made circular. Furthermore, in this embodiment the extension element 220 consists of two layers of foil 224a and 224b that are welded along their sides to form an enclosure 223 for the foam 228. The two layers of foil 224a, 224b are perforated to provide gas-inlets 226 in the gas-inlet portion 225. The non-permeable portion 227 also appears from the figure.

Figure 5:
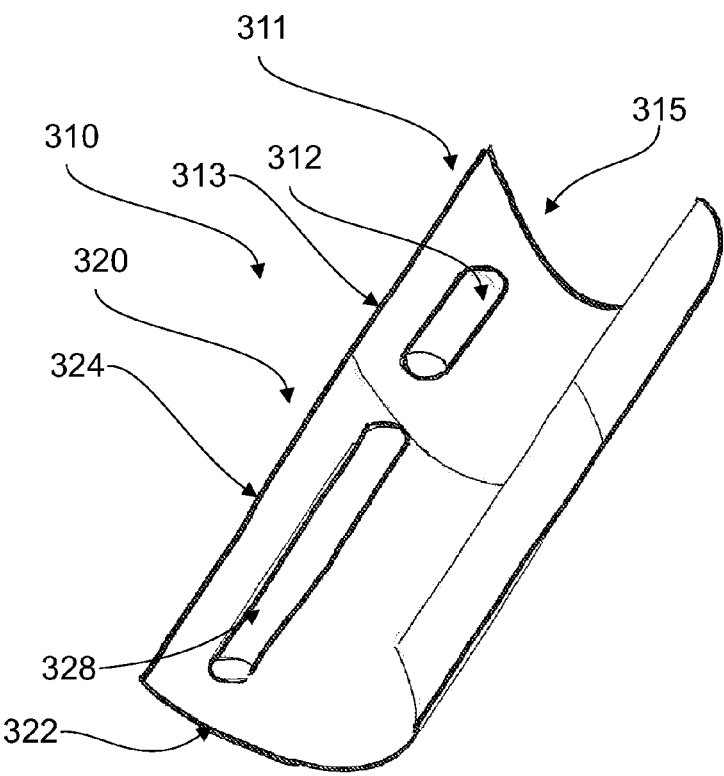
FIGS. 5 and 6 illustrate tube-like filter constructions.
Figure 6:
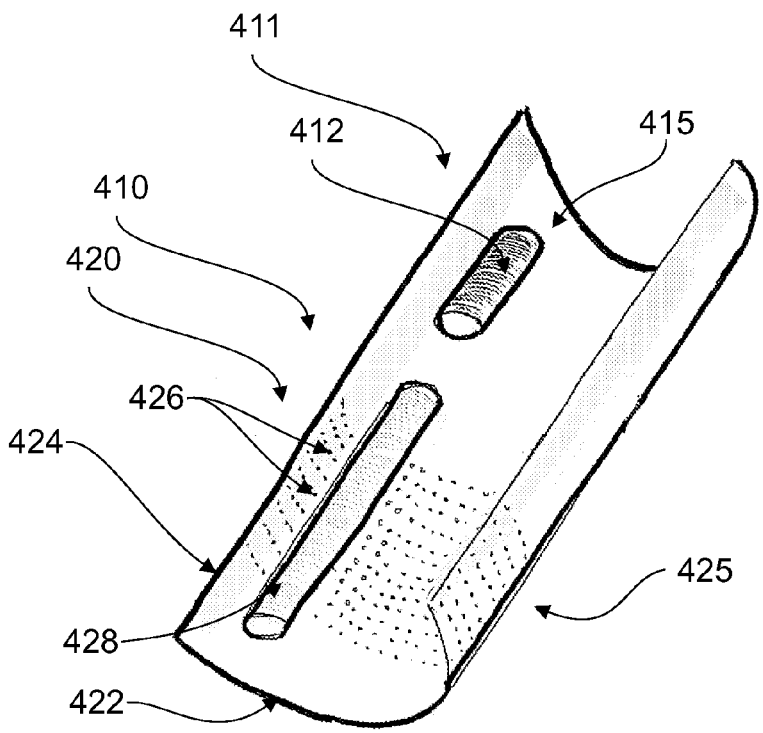

FIGS. 5 and 6 illustrate two examples of tube like filter constructions. In FIG. 5, the filter construction 310 comprises a net-foil 324 in the extension element 320 and in FIG. 6, the filter construction 410 comprises a perforated foil 424 in the extension element 420. Thus the gas-inlets 426 appear clearly in FIG. 6, while they cannot be seen in FIG. 5 because they are too small. The deodorising element 311, 411 comprises a carbon-impregnated impregnated tubular foam element 312, 412. The extension element 320, 420 comprises a foam element 328, 428. In the filter construction 310 in FIG. 5, the foil 313 at the deodorising element 311 is a gas- and liquid impermeable foil, which is welded to the net-foil 324. Alternatively, the net-foil can extend all the way at the deodorising element and be provided with an extra impermeable foil layer. The filter construction 310 is made by enclosing the foam elements 312 and 328 in the foils 324, 313 and then welding the combined foils 324, 313 in the length direction. Following this, the foils are closed at the second end 322 of the extension element. The opposite end of the filter construction is left open to provide for the gas-outlet 315.

In the filter construction 410, the foil 424 may extend past the deodorising element 411. It is only perforated at the gas-inlet portion 425 of the extension element. The foil 424 may be welded along the length to enclose both foam element 412 and 428. Finally, it may be welded at the second end 422 of the extension element. The gas-outlet 415 is provided in the opposite end of the filter construction.

The invention claimed is:

1. An ostomy bag comprising:
a pouch including a front wall and a rear wall,
a waste inlet opening formed in the rear wall to receive the output from a stoma,
a vent opening formed in the pouch,
a filter construction including a deodorising element and an extension element coupled to the deodorizing element,
the deodorising element having the gas outlet communicating with the vent opening,
the deodorising element connected to the pouch and to a first end of the extension element, where the extension element forms an enclosure and includes two opposed side edges that extend from the first end to a second end of the extension element, where a direction from the first end to the second end defines a longitudinal direction of the extension element,
the enclosure of the extension element is formed of a gas and liquid impermeable material and includes a gas-inlet portion including a plurality of gas-inlet holes formed in the gas and liquid impermeable material and a non-permeable portion without holes formed in the gas and liquid impermeable material;
the gas-inlet holes are oriented in a transverse direction across the gas-inlet portion transverse to the longitudinal direction of the extension element with a first plurality of gas-inlet holes formed through a first side of the extension element and a second plurality of gas-inlet holes formed through a second, opposite side of the extension element, where the gas-inlet portion of the extension element is separated from the deodorizing element by the non-permeable portion, and the gas-inlet portion is buoyant and adapted to float relative to the output from the stoma;
wherein the gas-inlet portion of the extension element is not coupled to the pouch.

2. The ostomy bag according to claim 1, wherein the extension element comprises a foil-element or an element made of non-woven material.

3. The ostomy bag according to claim 1, wherein a foam material is enclosed in the enclosure.

4. The ostomy bag according to claim 1, wherein the extension element comprises a tube-element.

5. The ostomy bag according to claim 1, wherein a separate buoyant element is attached to the second end of the extension element.

6. The ostomy bag according to claim 1, wherein a rim of the filter construction is attached at a contour of the ostomy bag.

7. The ostomy bag of claim 1, wherein the extension element comprises two elongate foil elements that are welded together at the two opposed side edges and at the second end.

8. The ostomy bag of claim 1, wherein the extension element comprises one foil element folded upon itself and welded at the two opposed side edges and the second end.

9. The ostomy bag of claim 1, wherein a distance from any one of the first and second plurality of gas-inlet holes to the first end of the extension element is at least 3 cm.

10. The ostomy bag of claim 1, wherein the gas-inlet portion is cantilevered from the deodorizing element.

11. The ostomy bag of claim 1, wherein the enclosure encloses atmospheric air.

12. The ostomy bag of claim 3, wherein the foam material has a density around 20 kg/m3.

13. The ostomy bag of claim 5, wherein the separate buoyant element comprises a foam element enclosed in a foil material.

14. The ostomy bag of claim 1, wherein the two opposed side edges and the second end of the extension element not coupled to the pouch.

15. The ostomy bag of claim 1, wherein the first end of the extension element is connected to the pouch.

16. The ostomy bag of claim 1, wherein the gas outlet of the filter construction is aligned with the vent opening.

* * * * *